(12) United States Patent
Heiniger et al.

(10) Patent No.: US 7,862,778 B2
(45) Date of Patent: Jan. 4, 2011

(54) FLUID SYSTEM COMPRISING A SAFETY DEVICE

(75) Inventors: Hanspeter Heiniger, Lotzwil (CH); Stefan Jost, Mühleberg (CH); Roger Siegenthaler, Münsingen (CH); Heinz Wuethrich, Worblaufen (CH)

(73) Assignee: Roche Diagnostics International AG, Steinhausen (CH)

( * ) Notice: Subject to any disclaimer, the term of this patent is extended or adjusted under 35 U.S.C. 154(b) by 1187 days.

(21) Appl. No.: 11/328,720

(22) Filed: Jan. 10, 2006

(65) Prior Publication Data

US 2006/0177351 A1 Aug. 10, 2006

Related U.S. Application Data

(63) Continuation of application No. PCT/EP2004/007383, filed on Jul. 6, 2004.

(30) Foreign Application Priority Data

Jul. 16, 2003 (DE) ................. 103 32 289

(51) Int. Cl.
*B01L 3/02* (2006.01)

(52) U.S. Cl. .................. 422/100; 422/102; 422/104; 422/58; 422/103; 422/68.1; 210/198.2; 210/656

(58) Field of Classification Search ........... 422/68.1, 422/100; 137/828; 435/91.2
See application file for complete search history.

(56) References Cited

U.S. PATENT DOCUMENTS

| 6,379,929 B1* | 4/2002 | Burns et al. ............... 435/91.2 |
| 6,521,188 B1 | 2/2003 | Webster |
| 2003/0083686 A1 | 5/2003 | Freeman et al. |
| 2004/0007275 A1* | 1/2004 | Hui Liu et al. ............. 137/828 |

FOREIGN PATENT DOCUMENTS

WO    WO 02/18785 A1    3/2002

OTHER PUBLICATIONS

Guerin et al. Micro Electro Mechanical Systems, 1998. MEMS 98. Proceedings., The Eleventh Annual International Workshop on Publication Date: Jan. 25-29, 1998.*

* cited by examiner

*Primary Examiner*—Jill Warden
*Assistant Examiner*—Sally A Sakelaris
(74) *Attorney, Agent, or Firm*—Dinsmore & Shohl LLP (57) ABSTRACT

A fluid system that includes a flow system for a liquid having an inlet, an outlet, at least one fluid line extending from the inlet to the outlet and an electrically activatable melting device, wherein activation of the melting device causes melting, which interruptes, stops or diverts a flow of the fluid through the flow system. In one embodiment, the fluid system may be used in a device for measuring blood sugar.

34 Claims, 6 Drawing Sheets

FLUID SYSTEM COMPRISING A SAFETY DEVICE

CROSS-REFERENCE TO RELATED APPLICATIONS

This application is a continuation of International Patent Application No. PCT/EP2004/07383, filed Jul. 6, 2004, which claims priority to German Patent Application No. DE 103 32 289.2, filed on Jul. 16, 2003, and the entire content of both applications is incorporated herein by reference.

BACKGROUND

The present invention relates to devices for delivering, administering or dispensing substances, and to methods of making and using them. More particularly, the present invention relates to a fluid system comprising a flow system for the passage of a fluid wherein a flow in the flow system may be changed if an event occurs. For example, in one embodiment, the invention relates to a fluid system for a device for blood sugar determination in which a flow of a fluid is interrupted, stopped or diverted in the event of a malfunction of the blood sugar determination device.

Fluid systems in which fluids are conveyed through a flow system, having an inlet and an outlet for the liquid and one fluid line or a multiplicity of fluid lines leading from the inlet to the outlet, are used in a variety of technical fields. In medical technology in particular, a reliable function of such a fluid system is important because a malfunction of the fluid system poses a number of risks to the user or patient. For example, if a fluid active substance, for instance insulin, is being transported, a malfunction can lead to an inadequate dosage or an overdosage of the active substance. When a measurement solution is being transported, a malfunction can lead to imprecise or false measurements, or the patient may be put in danger because of an incompatibility of the measurement solution.

In order to ensure user safety, the fluid system can have a safety device which, by measuring a control parameter, for example the pressure in the fluid system, registers a malfunction of the fluid system and thereupon interrupts the flow of liquid in the flow system.

Such a safety device is desirable, for example, in a measurement method in which a measurement probe with a dialysis membrane is introduced into a patient's tissue and a measurement liquid is guided through the measurement probe. One example of a measurement method of this kind is the determination of blood sugar values of a patient suffering from diabetes. The measurement liquid may, for example, be introduced into the probe from an ampoule by way of a fluid system. In order to measure a blood sugar value, the measurement liquid is conveyed at a constant pressure through the flow system of the probe. The probe is introduced into the patient's body tissue in such a way that the measurement liquid comes into interaction with the environment of the tissue via the dialysis membrane. If, for example, a leak were to occur in the dialysis membrane inside the tissue, the measurement liquid would flow out of the flow system and into the tissue. A malfunction of this kind can be determined, for example, by the associated drop in pressure or complete loss of pressure in the flow system. In the event of such a malfunction, it is desirable, at least for the safety of the patient, to suppress the stream of measurement liquid in the flow system, so that no measurement liquid gets into the tissue.

SUMMARY

It is an object of the present invention to provide a fluid system which has safety features for the event of a malfunction of the fluid system, avoids undesired escape of a fluid in the event of a leakage, increases the level of safety when using the fluid system, and can easily be provided on or in the fluid system.

It is a further object of the present invention to make available a device for measuring blood sugar values in which, in the event of a malfunction of the fluid system for a measurement liquid, a safety feature is provided such that no amount of measurement liquid or only a negligible amount of measurement liquid can pass into the body tissue.

According to embodiments of the present invention, a fluid system flow system includes an inlet, an outlet, and at least one fluid line extending from the inlet to the outlet. The outlet may open into a collecting receptacle or into a conduit system attached to the fluid system, for example. The fluid lines may, for example, be provided as tubes or hoses. The invention may be implemented in a fluidic chip having a channel system for small amounts of fluid. In certain embodiments the channel system fluid lines may be designed as channels in the form of depressions in a solid support, which depressions are closed off on their open face, for example, by a laminate film. Using a laminate film, the melting device may melt a hole in the laminate material enabling fluid to flow through a hole in the laminate material and into a runoff, described below.

According to embodiments of the invention, the fluid system may be characterized by an electrically activatable melting device, the melting of which may cause a flow of the fluid through the flow system to be interrupted, stopped, or the fluid flow to be diverted. By means of the melting of the melting device, a fluid line may be blocked so that through-flow of the fluid is no longer possible. However, the melting may form a runoff which, for example, consists of an opening in at least one of the fluid lines. The runoff may open into a diversion channel which, before activation of the melting device, has no fluidic connection to a fluid line.

The melting device, according to some embodiments of the present invention may, for example, be formed exclusively by an electrical conductor which melts when an excess current is applied, i.e. when a current is applied which is greater than is permitted by the dimensioning of the electrical conductor. By means of this melting of the electrical conductor, a fluid line may be blocked, or an opening may be formed as a runoff in a fluid line. In addition, according to certain embodiments, the melting device may include a meltable material which may be melted by an electrical conductor. When a current is passed through the electrical conductor, the latter is heated and any surrounding material may melt, as a result of which it is possible to establish a blockage or a runoff in a fluid line. In this case, the electrical conductor is not required to melt in order to stop, divert, or interrupt fluid flow.

In a fluid system with a melting device, according to embodiments of the invention, it is possible, in the event of a malfunction of the fluid system, for the flow of liquid to be interrupted or diverted by activation of the melting device. A flow of the fluid into undesired areas may be stopped immediately after detection of the malfunction. For example, in a measurement method with a fluid circuit, the delivery of measurement liquid or the administration of a fluid may be terminated at a specific site. In this way, the safety of a person using the fluid system may be promoted.

To form the runoff line, according to certain embodiments of the invention, the electrical conductor may be arranged bordering on a fluid line. The routing of the electrical conductor on the fluid line may have many configurations. For example, the electrical conductor may be routed in a spiral formation about a tubular fluid line, may bear at one or multiple sites on the fluid line, or may pass through a fluid line. In another example, the electrical conductor may form part of the wall of the fluid line. In yet another example, the electrical conductor may be coupled to a plurality of sites along said fluid line. The electrical conductor may be positioned at a site on a fluid line which favorable for forming a runoff. The electrical conductor passes energy, and in order to activate the melting device, an electric current greater than a maximum current for which the electrical conductor is designed or dimensioned is passed through the electrical conductor. In response to the excess current, the electrical conductor melts, or it heats to such an extent that the material surrounding the conductor melts. Accordingly, a runoff on the fluid line may be generated by means of an opening or a leak arising in the fluid line as a result of the melting, or by means of the partial area of the fluid line formed by the electrical conductor being laid open by the melting.

The electrical conductor may have a constriction area as the melt site. The constriction may be formed, for example, by a narrowed point in a band-shaped conductor or by a site of lesser diameter in a wire-like conductor. The narrowed site has an increased electrical resistance. On application of an excess current, the electrical conductor heats up first at the constriction. The constriction of the electrical conductor may accordingly be arranged at a site of the fluid line intended for the runoff.

In order to determine a malfunction of the fluid system and then to be able to activate the melting device, a pressures sensor for measuring the pressure of the fluid inside the flow system may be provided. At a defined critical pressure, for example, in the event of a defined drop in pressure or a complete loss of pressure, the melting device may be activated automatically. Accordingly, the fluid system may be provided with a battery and a control means. The melting device may be activated in the event of a drop in pressure or loss of pressure in the flow system. A drop in pressure or loss of pressure can be caused, for example, by a leak in the flow system, through which leak the fluid is able to pass into undesired areas. As a result of the leak, the pressure in the flow system collapses or at least drops sharply. If the pressure drops below a minimum value, the melting device may be activated by an excess current so that the runoff is generated and the fluid is conveyed out of the flow system. It may also be possible to use other parameters, such as the temperature of the fluid, as the critical variable for activation of the melting device or to manually activate the melting device as and when desired. For example, the melting device may be activated in response to detecting a predetermined temperature, or a predetermined change in temperature of the fluid in the flow system.

In another embodiment of the present invention, a fluid system may be configured as a microdialysis probe or a device for measuring blood sugar values. For example, the microdialysis probe may include a semi-permeable fluid line, which may be capable of interacting with fluids outside of said fluid line. According to embodiments of the present invention, the fluid line may be closable upon activation of the melting device in order to prevent leakage out of the semi-permeable fluid line.

According to yet another embodiment of the present invention, a fluid system may include a flow system for a fluid, having an inlet, an outlet, at least one flow path extending generally from the inlet to the outlet, and a device coupled to the flow path. The device may be capable of changing state or changing in one or more characteristics upon receiving one of a force, stimulus or communication, where, upon receipt of said suitable force, stimulus or communication, the device interrupts, stops or diverts a flow of the fluid in the flow path.

BRIEF DESCRIPTION OF THE DRAWINGS

FIG. 2 (FIGS. 2a, 2b, and 2c) illustrates an exploded view of a fluidic chip with a melting device, according to one embodiment of the present invention;

FIG. 4 (FIGS. 4a and 4b) is an illustration of an exploded view of a fluidic chip with a melting device according to the present invention.

DETAILED DESCRIPTION

With regard to fastening, mounting, attaching or connecting the components of devices of the present invention, unless specifically described as otherwise, conventional fasteners such as screws, rivets, toggles, pins and the like may be used. Other fastening or attachment means appropriate for connecting components include friction fitting, adhesives, welding and soldering, the latter particularly with regard to electrical or processing components or systems of the devices. Any suitable electronic, electrical, communication, computer or processing components may be used, including any suitable electrical components and circuitry, wires, wireless components, sensors, chips, boards, micro-processing or control system components, software, firmware, hardware, etc.

Figure 1:
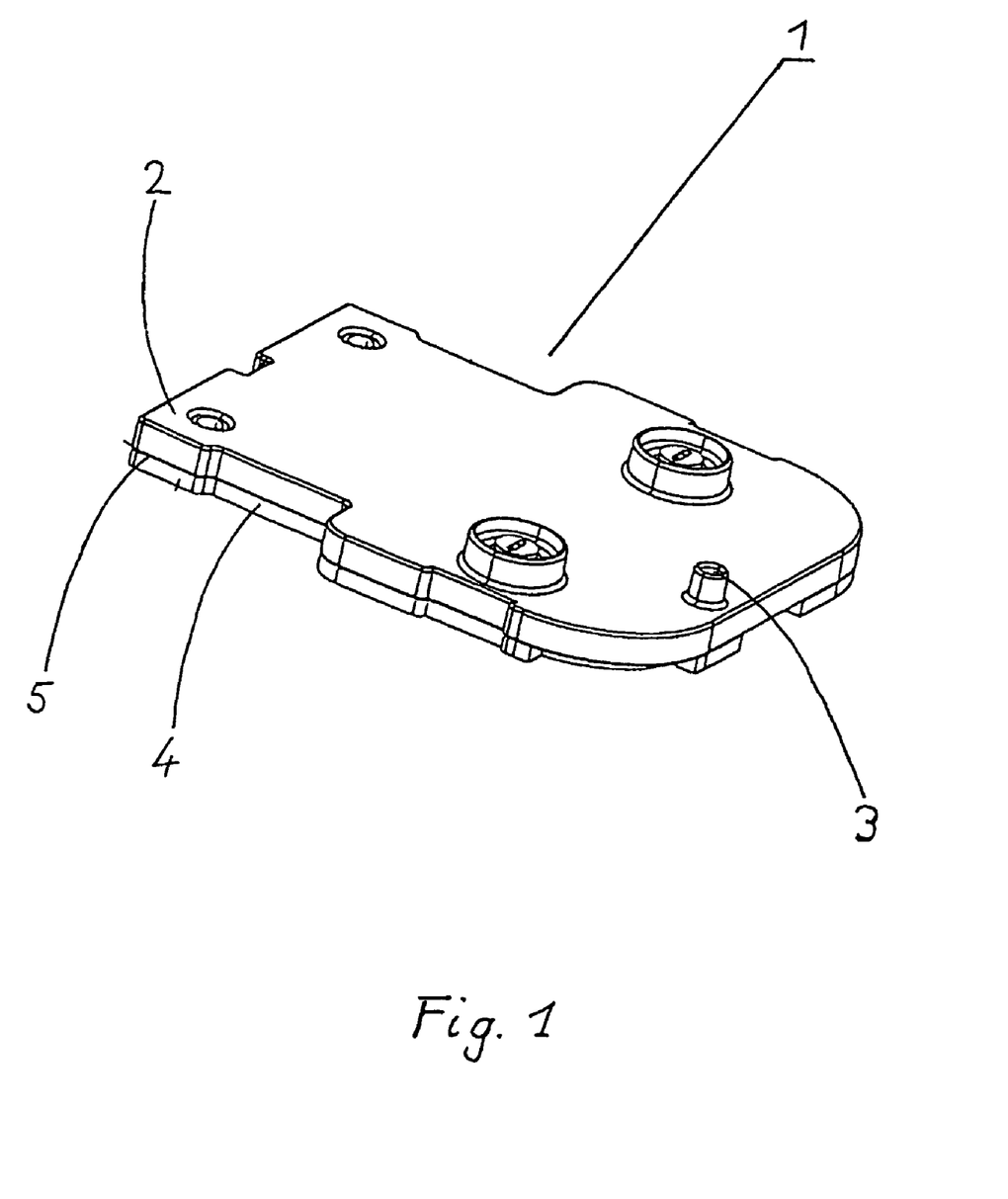
FIG. 1 illustrates a perspective view of a fluidic chip.

FIG. 1 shows a fluidic chip 1, as can be used in various appliances and apparatus, and in particular for medical and therapeutic applications in which a flow or an administration of a fluid is necessary. Such a fluidic chip may be suitable for conveying small quantities of a fluid. The fluidic chip 1 is composed of an upper support plate 2, with an inlet 3 for the fluid on its top face, and of a lower support plate 4. Provided between the upper support plate 2 and the lower support plate 4 there is a laminate film 5 made of meltable material.

Figures 2, 2A:
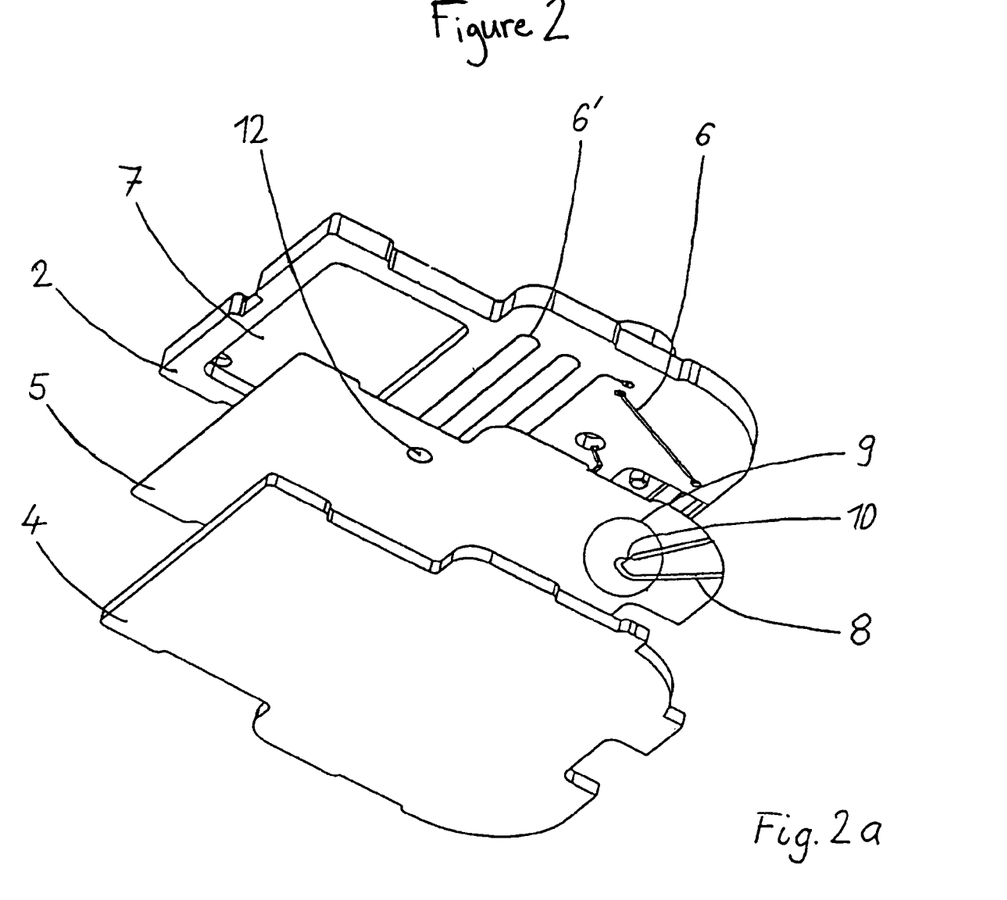
Figure 2B:
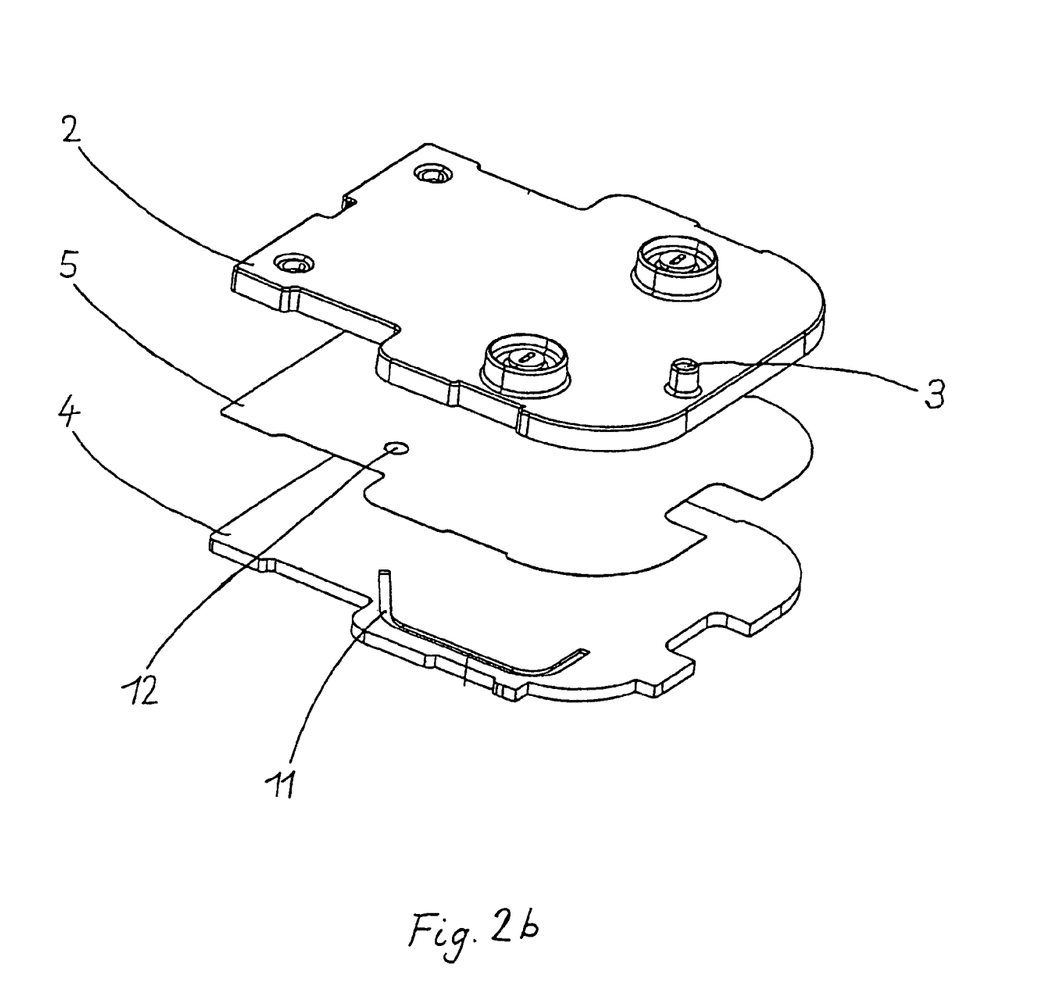
Figure 2C:
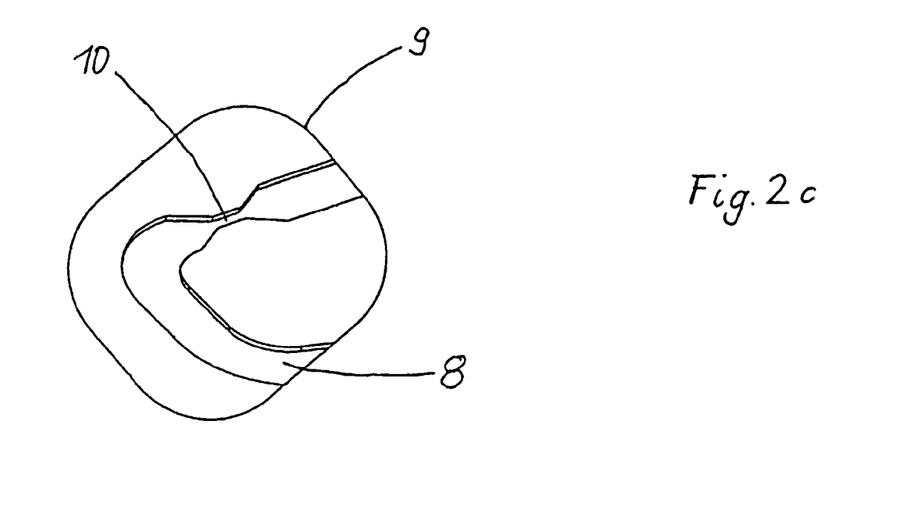

One embodiment of a fluid system according an embodiment of the present invention is shown in FIG. 2 (FIGS. 2a, 2b, and 2c). In the figure, the fluidic chip is depicted in an exploded view in order to show the fluid system which is accommodated in the inside of the fluidic chip and which comprises a flow system and a melting device according to the invention. In the upper support plate 2, on its face lying to the inside of the fluidic chip 1, fluid lines 6 and 6' are provided as depressions in the support plate 2. The fluid line 6 is connected to the inlet 3 and therefore forms a fluidic connection from the inside of the fluidic chip 1 to the top face thereof. The fluid lines 6 and 6' are connected to one another, and the fluid line 6' has an outlet (not shown) which opens into a collecting receptacle 7. The collecting receptacle 7 is formed as a large trough-like depression let into the inner face of the upper support plate 2 and it can have a closable output from the fluidic chip 1. The inlet 3, the fluid lines 6 and 6' and the outlet into the collecting receptacle 7 form the flow system for a fluid through the fluidic chip. Of course, it is also possible to provide a fluid line on the fluidic chip, which line extends out of the fluidic chip 1 into the outer environment and back into the fluidic chip. In the outer environment, the fluid can interact with the environment, for example via a semipermeable membrane on the fluid line, as is done, for example, when measuring blood sugar.

The laminate film 5 covers the entire inner face of the upper support plate 2 and thus closes off the channel depressions in the support plate 2 for the fluid lines 6 and 6' on the inner face of the support plate 2. An electrical conductor 8 is arranged on the laminate film 5 in such a way that it extends from an edge of the laminate film 5 into an area 9 and from there back to the edge of the laminate film. The area 9 lies over the fluid line 6 so that the electrical conductor 8 adjoins the fluid line 6. According to one embodiments, the electrical conductor 8 may be routed from different sides to the area 9 over the fluid line 6. According to this embodiment, an input line and an output line for supplying the electrical conductor with electric current may be provided and may be accessible from outside of the fluidic chip 1. The area 9 is shown in an enlarged view in FIG. 2c, which depicts electrical conductor 8 as being arranged in a band shape on the laminate film 5 and having a constriction 10 at the site where it adjoins the fluid line 6. In the area of the constriction 10, the electrical conductor 8 has a smaller band width than in the rest of the conductor band.

FIG. 2b shows the inner face of the lower support plate 4 of the fluidic chip 1, where a depression is provided as diversion channel 11. The diversion channel 11 is closed off by the laminate film 5 when the fluidic chip 1 is in the assembled state. The diversion channel 11 initiates on the lower support plate 4, at a site bordering the constriction 10 of the electrical conductor 8, and leads to a site underneath the collecting receptacle 7. The diversion channel 11 opens into the collecting receptacle 7 via an opening 12 in the laminate film 5.

In the assembled state of the fluidic chip 1, the fluid system, according to one embodiment of the invention, is made up of the above-described flow system, of the electrical conductor 8 with the constriction 10 as melting device, and of the diversion channel 11 and the collecting receptacle 7. When the fluid system is operating correctly, a fluid is conveyed through the inlet 3 and into the fluidic chip, the fluid flows through the fluid lines 6 and 6' and through the outlet into the collecting receptacle 7. If the fluid system malfunctions, particularly if there is a drop in pressure or loss of pressure in the flow of fluid in the fluid lines 6 and 6', an electric current is guided through the electrical conductor 8 at a level for which the constriction 10 of the electrical conductor 8 is not adequately dimensioned, i.e. an excess current is generated on the electrical conductor. Because of the excess current, the electrical conductor 8 melts at the constriction 10 and thereby generates a runoff in the form of a hole, or a leak, in the laminate film 5 in the area bordering the fluid line 6. According to this embodiment of the invention, the constriction 10 forms a melt area of the melting device. By means of the hole generated in the laminate film 5, a fluidic connection may be established to the diversion channel 11 in the lower support plate 4, such that fluid is routed from the fluid line 6 into the diversion channel 1. The diversion channel 11 may be dimensioned so that the fluid flowing into the fluid line 6 through the inlet 3 may be accepted by the diversion channel 11 through the opening 12 at the melt site and conveyed onward. Instead of passing through the fluid lines 6 and 6' of the flow system, the fluid then flows through the diversion channel 11 to the opening 12 and into the collecting receptacle 7. According to certain embodiments of the present invention, the flow of fluid may thus be interrupted, stopped, or reduced by the electrical activation of the melting device.

The fluidic chip 1, according to one embodiment of the invention, may form a closed system, i.e. in the event of a malfunction, in which the flow of the fluid is interrupted by the activation of the melting device, the fluid does not flow out of the fluidic chip 1, but instead may be diverted within the fluidic chip 1 and pass into the collecting receptacle 7. According to this exemplary embodiment, the fluid does not leave the fluid system, which otherwise could result in damage to an appliance or a risk to a user or patient.

Figure 3:
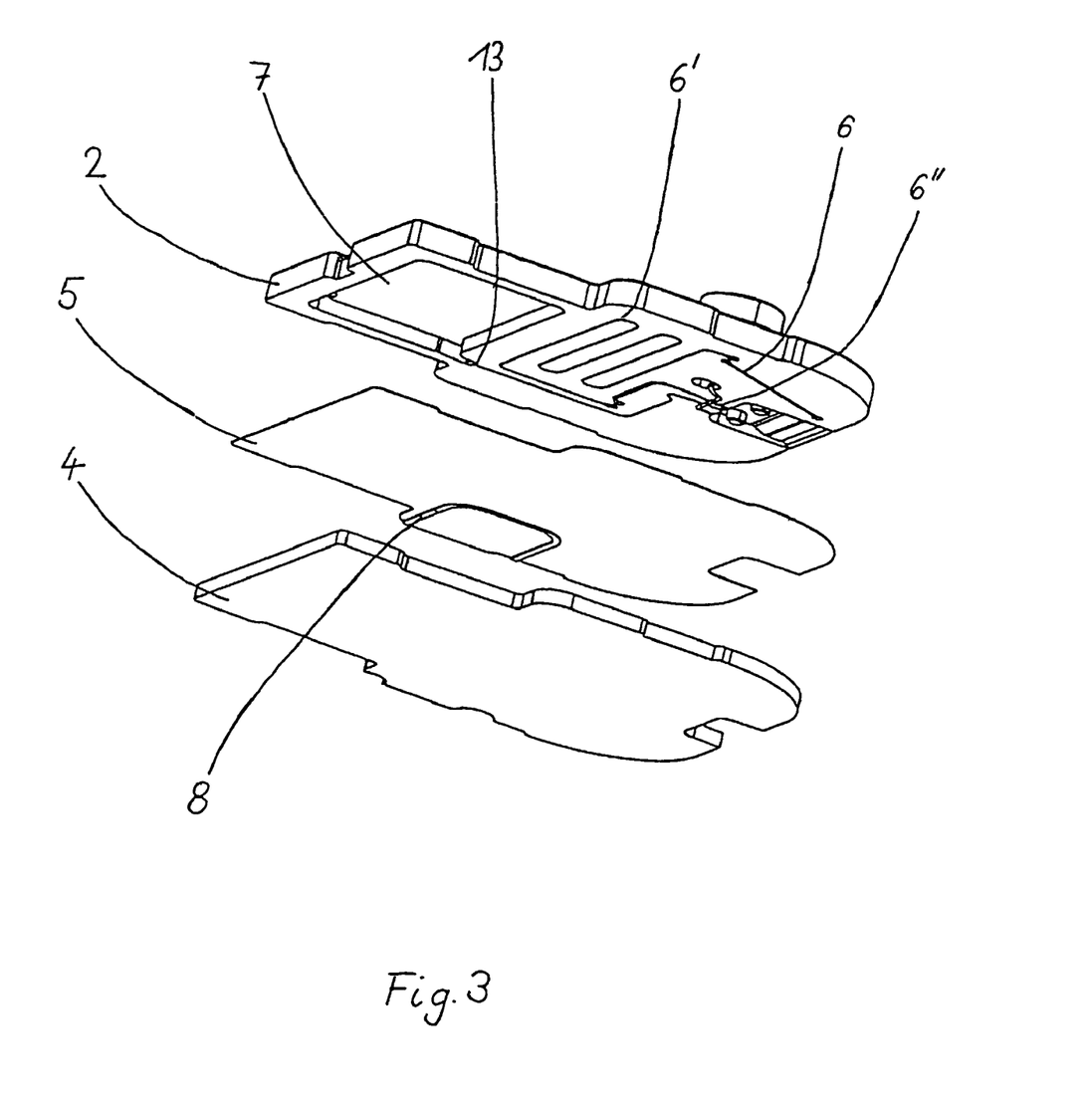
FIG. 3 illustrates an exploded view of a fluidic chip with a melting device according to an embodiment the present invention.

FIG. 3 illustrates another embodiment of a fluid system according to the present invention, in the form of a fluidic chip 1. The upper support plate 2 includes an inlet 3 (not shown), fluid lines 6, 6' and an outlet to a collecting receptacle 7, as in the embodiment shown in FIG. 2. The figure also shows fluid lines 6" which permit attachment to a line in an outer area outside the fluidic chip 1. According to this exemplary embodiment, provided on the laminate film 5 may be an electrical conductor 8. The electrical conductor 8 may initiate at a lateral edge of the laminate film 5, be routed across a central area of the film, and terminate at the edge of the laminate film 5. According to this exemplary embodiment, no further measures for the fluid system are provided on the lower support plate 4, and instead the lower support plate 4 serves for stable attachment of the fluidic chip 1.

According to embodiments of the present invention, in the assembled state of the fluidic chip 1, the electrical conductor 8 may border the fluid line 6' at several sites. Upon applying an electric current to the electrical conductor 8, the laminate film 5 may melt at the areas covered by the electrical conductor 8, as a result of which the fluid line 6' is blocked at the sites bordering the electrical conductor 8. In some instances, however, it may be adequate to block the fluid line 6' at one site. Accordingly, a constriction may be provided in the electrical conductor 8, and upon melting constriction areas in conductor 8, fluid in fluid line 6' may be blocked, and the flow of the fluid through the flow system may be stopped. A blockage may be produced in an area of the fluid line 6' lying before the fluid line 6", such that a flow into a line lying outside the fluidic chip may be stopped. This may allow the suppression of an undesired escape of a fluid from the fluidic chip 1 in the event of a malfunction of the fluid system.

Figures 4, 4A:
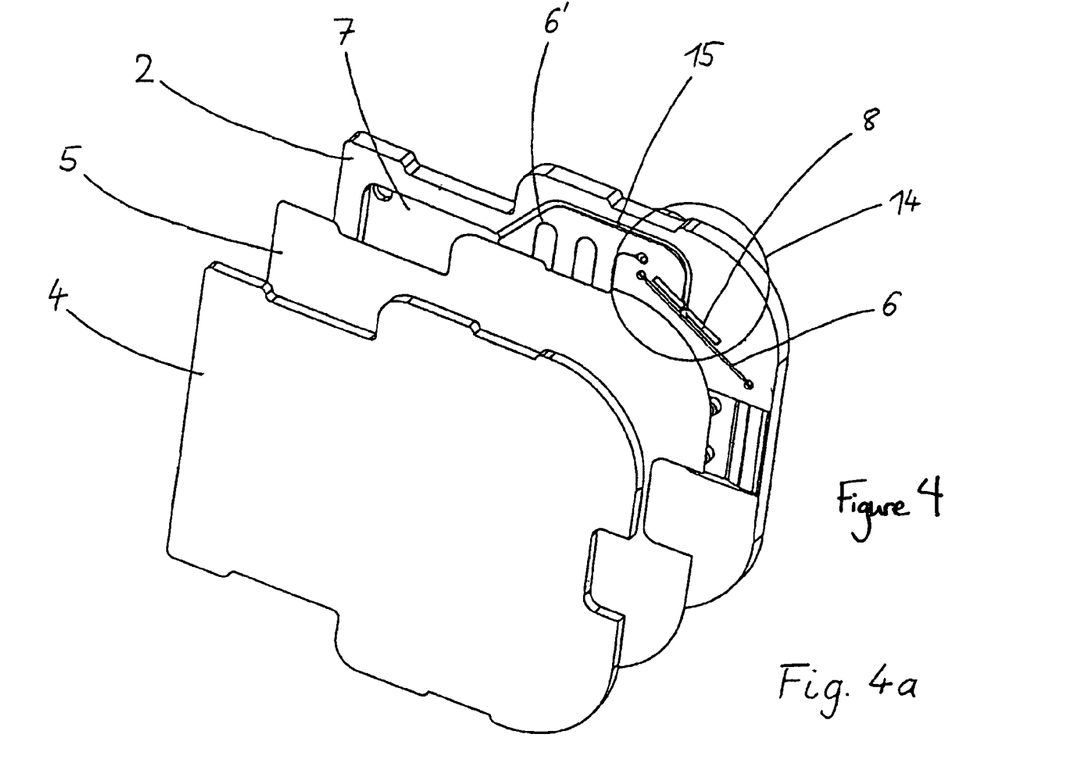
Figure 4B:
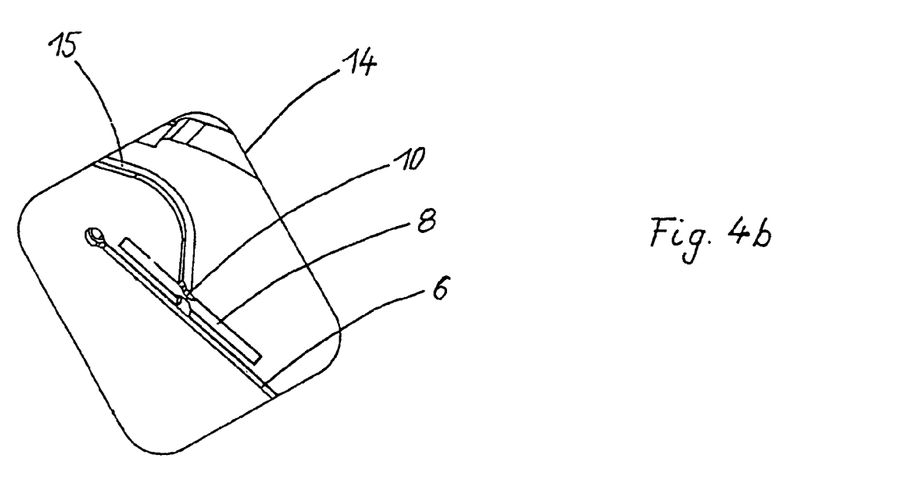

FIG. 4 (FIGS. 4a and 4b) depicts another embodiment of a fluid system, in the form of a fluidic chip 1, according to the present invention. The structure of the upper support plate 1 may be analogous to that of the embodiment shown in FIG. 2, but may further include a diversion channel 15 and an area 14 in which a melting device may be provided. The melting area 14 is shown enlarged in FIG. 4b. According to FIG. 4, from the fluid line 6, the diversion channel 15 branches off as a depression in the upper support plate 2 and leads to the collecting receptacle 7. Between the fluid line 6 and the diversion channel 15, an electrical conductor 8 may be arranged in such a way that it closes off a fluid connection between the line 6 and the channel 15, i.e. separates the line 6 from the channel 15. In the separation area between the fluid line 6 and the diversion channel 15, the electrical conductor 8 includes a constriction 10 having a smaller cross-sectional surface area than at the adjoining areas. In the embodiment shown, the electrical conductor 8 is integrated parallel to the fluid line 6 into the inner surface of the upper support plate 2. The two ends of the electrical conductor 8 form a feed line and an output line for an electric current and may be routed through the upper support plate 2 and outward to the outer surface of the support plate 2.

According to embodiments of the present invention, the laminate film 5 may be cut to size to match the shape of the upper support plate, and in certain embodiments, no further arrangements for the fluid system are needed on the laminate film 5. In certain additional embodiments, additional arrangements for the fluid system on the lower support plate 4 may also not be required.

According to some embodiments of the present invention, by the electrical activation of the melting device, i.e. by delivering an excess current to the electrical conductor 8, the electrical conductor 8 melts at the constriction 10 and frees the fluid connection between the fluid line 6 and the diversion channel 15. By melting the electrical conductor 8, a runoff may be produced for the fluid from the flow system. The diversion channel 15 may be dimensioned in such a way that the fluid introduced through the inlet 3 is led off completely via the diversion channel 15 and an amount of fluid flowing through the fluid line 6 may be ignored.

The fluid system of FIG. 4 forms a kind of closed system in accordance with the embodiment in FIG. 2. In the embodiment according to FIG. 2, and in the embodiment according to FIG. 3, the electrically activatable melting device according to the invention may include an electrical conductor and a laminate film which can melt when an electric current is passed through the electrical conductor. An interruption or discontinuation of the flow of the fluid through the flow system of the fluid system may therefore be obtained by melting the laminate film. The electrical conductor does not necessarily have to melt itself, and may instead melt an opening in the laminate film that is large enough to serve as a runoff for the fluid from the flow system, or sufficient laminate film melts to block a fluid line. However, according to some embodiments, when the melting device is activated, the electrical conductor itself also melts, in addition to the laminate film. In order to block a fluid line, the melted material from the laminate film and electrical conductor jointly or from the laminate film alone or from the electrical conductor alone may block a fluid line.

In the embodiment of the present invention according to FIG. 4, the laminate film may not be required to be meltable. Instead, a runoff for the fluid from the flow system may be obtained by melting the electrical conductor. According this embodiment, the electrically activatable melting device may be formed by the electrical conductor, without an additional meltable material having to be provided.

Figure 5:
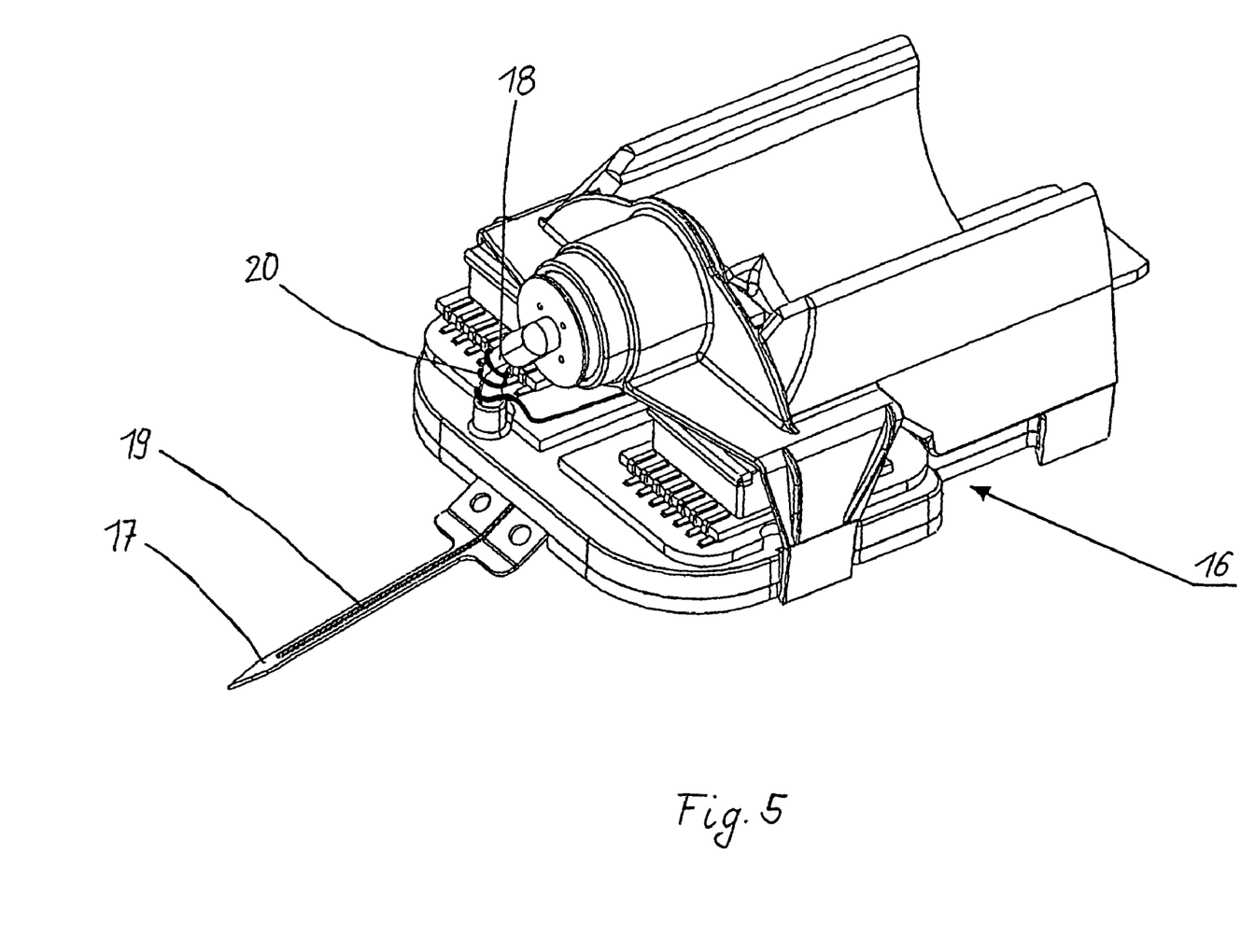
FIG. 5 is an illustration of a perspective view of a device for blood sugar measurement comprising a fluid system according to the present invention.

FIG. 5 shows a device for blood sugar measurement in which a fluid system is used, according to the present invention. The blood sugar measurement device includes a housing 16 from which a microdialysis probe 17 protrudes. In addition to various other devices for blood sugar measurement, a fluid system according to the present invention may be arranged in or on the housing 16. From a fluid reservoir located inside the housing 16, fluid may be conveyed through a fluid line 18 to a fluid line 19 which is routed, in a slit located inside the probe 17, to the tip of the probe and from there back into the housing 16. Through the flow system, a measurement solution may be conveyed from the housing 16 through the fluid line 19 with the aid of the probe 17 into the tissue of a patient and then conveyed back again. The fluid line 19 may include a semi-permeable membrane so that the measurement solution may interact with the environment surrounding the tissue. In the event of a malfunction of the fluid system, for example in the event of a leak in the fluid line 19, it may be possible for the measurement solution to pass from the flow system into the tissue. This can pose a risk to the patient, and the blood sugar measurement will not be performed correctly.

A wire-like electrical conductor 20 may be arranged in a spiral formation around the fluid line 18 on the housing 16 in such a way that, along its windings, it borders the fluid line 18. In a malfunction of the fluid system in the measurement device as described above, the pressure in the fluid line 19 drops sharply or is lost altogether. This change in pressure may, for example, be recorded by a pressure sensor inside the device and the electrically activatable melting device in the form of the electrical conductor 20 may thus be activated. For example, an excess current may be passed through the electrical conductor 20 from a battery or capacitor arranged in the housing. The electrical conductor 20 thus melts and produces a runoff in the fluid line 18, by means of an opening or leak being melted into this line. For embodiments where the fluid line is melted into, the material used for the fluid line should, at least one portions, be meltable.

The present invention has been described on the basis of a fluid system for a medical or pharmaceutical device. However, a fluid system according to the invention may also be used in other devices, for example in microscopic detection methods, crystallization methods or other scientific and technical methods. In addition, according to certain embodiments, the melting device of the present invention comprises a meltable material which may be melted by an electrical conductor and/or electricity. Such a material includes, for example, thermoplastics, metals, or any suitable material capable of melting. It should be appreciated that any suitable material (e.g., shape-memory material) capable of changing state or changing in one or more characteristics upon receiving a suitable force, stimulus or communication (e.g., current, heat, cold, RF, chemical, etc.) could be used. For example, a shape-memory material could be used.

Embodiments of the present invention, including preferred embodiments, have been presented for the purpose of illustration and description. They are not intended to be exhaustive or to limit the invention to the precise forms or steps disclosed. The embodiments were chosen and described to provide the best illustration of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for measuring blood sugar values, comprising:
a first support plate and a second support plate, at least one of the first support plate and the second support plate having an inner face including a fluid system formed as depressions in the inner face, the fluid system comprising an inlet, an outlet and at least one fluid line extending from the inlet to the outlet;
an electrical current supply device; and
a meltable component comprising a film positioned between the first and second support plates such that it extends over at least a portion of the inner face and beyond the fluid line, and an electrical conductor integral with the film, wherein
the electrical conductor is electrically coupled to the electrical current supply device, and
the meltable component is positioned with respect to the at least one fluid line such that electrical current passing through the electrical conductor melts the meltable component thereby causing a flow of the fluid through the flow system to be interrupted, stopped or diverted.

2. The device for measuring blood sugar values according to claim 1, wherein said electrical conductor borders on said at least one fluid line.

3. The device for measuring blood sugar values according to claim 1, wherein said electrical conductor comprises a constriction area capable of melting.

4. The device for measuring blood sugar values according to claim 1, wherein said at least one fluid line is overlaps said electrical conductor at a plurality of sites along said fluid line.

5. The device for measuring blood sugar values according to claim 1, wherein said electrical current supply device is configured to send an excess current to said meltable component.

6. The device for measuring blood sugar values according to claim 1, further comprising a runoff for receiving fluid from the flow system generated by activation of the electrical current supply device, wherein the runoff is formed as a depression in an inner face of either or both of the first and second support plates.

7. The device for measuring blood sugar values according to claim 6, wherein said runoff is in fluid communication with a fluid collecting receptacle, the fluid collecting receptacle being formed as a tough-like depression in an inner surface of either or both of the first and second support plates.

8. The device for measuring blood sugar values according to claim 6, wherein said meltable component is configured to melt a hole in the film thereby enabling fluid to flow through said hole and into said runoff.

9. The device for measuring blood sugar values according to claim 1, wherein said electrical current supply device is configured to be activated automatically.

10. The device for measuring blood sugar values according to claim 1, further comprising a runoff, wherein said runoff is closed upon activation of said electrical current supply device.

11. The device for measuring blood sugar values according to claim 1, wherein the electrical current supply device is activated in the event of a drop in pressure or loss of pressure of the fluid flow in the flow system.

12. The device for measuring blood sugar values according to claim 1, wherein the electrical current supply device is activated in response to a predetermined change in temperature of the fluid in the flow system.

13. The fluid system according to claim 1, wherein the electrical conductor is meltable in response to activation of said electrical current supply device.

14. The device for measuring blood sugar values according to claim 1, wherein the flow system is configured as a fluidic chip.

15. The device for measuring blood sugar values according to claim 1, wherein the flow system is configured as a microdialysis probe.

16. The device for measuring blood sugar values according to claim 15, wherein said microdialysis probe comprises a semi-permeable fluid line, wherein said fluid line capable of interacting with fluids outside of said fluid line, and wherein said fluid line is closable upon activation of said electrical current supply device.

17. A device for measuring blood sugar values, comprising:
 a first support plate and a second support plate, at least one of the first support plate and the second support plate having an inner face including a flow system for transporting blood sugar measurement fluid, the flow system being formed as depressions in the inner surface, the flow system comprising:
  an inlet;
  an outlet; and
  at least one fluid line extending from the inlet to the outlet;
 an electrical current supply device; and
 a meltable component comprising a film and an electrical conductor, the film positioned between the first and second support plates such that it extends over at least a portion of the inner face and beyond the fluid line, wherein the electrical conductor is electrically coupled to the electrical current supply, and is modifiable from an initial state, in which measurement fluid flows through the fluid line flows, and an activated state, in which the electrical conductor melts the film thereby diverting measurement fluid away from the outlet; and
 a fluid runoff formed as a depression in either or both of the first and second support plates, wherein in the activated state, the fluid runoff receives the diverted fluid.

18. The device for measuring blood sugar values according to claim 17, wherein said runoff is in fluid communication with a fluid collecting receptacle, the fluid collecting receptacle being formed as a tough-like depression in an inner surface of either or both of the first and second support plates.

19. The device for measuring blood sugar values according to claim 17, further comprising another fluid line arranged outside of the flow system, the another fluid line fluidically coupled to the flow system, wherein in the initial state, fluid flows through the another fluid line, and in the activated state, fluid from the flow system is stopped from flowing through the another fluid line.

20. The device for measuring blood sugar values according to claim 17, wherein the meltable component further comprises an electrical conductor configured such that the film melts when an electric current is passed through the electrical conductor such that an opening in the film is formed and the fluid runoff receives fluid diverted through the opening.

21. The device for measuring blood sugar values according to claim 17, wherein the meltable component further comprises an electrical conductor which melts the film when an electric current is passed through the electrical conductor such that the melted film blocks the fluid line.

22. The device for measuring blood sugar values according to claim 17, wherein the meltable component further comprises an electrical conductor, wherein an electric current is passed through the electrical conductor in the activated state and melts the electrical conductor such that the melted conductor blocks the fluid line.

23. The device for measuring blood sugar values according to claim 20, wherein said at least one fluid line overlaps said electrical conductor at a plurality of sites along said fluid line.

24. The device for measuring blood sugar values according to claim 17, wherein the meltable component is activated in the event of a drop in pressure or loss of pressure of the fluid flow in the flow system.

25. The device for measuring blood sugar values according to claim 17, wherein the meltable component is activated in response to a predetermined change in temperature of the fluid in the flow system.

26. A device for measuring blood sugar values, comprising:
 a first support plate and a second support plate, at least one of the first support plate and the second support plate having an inner face including a flow system for transporting blood sugar measurement fluid, the flow system being formed as depressions in the inner surface, the flow system comprising:
  an inlet;
  an outlet; and
  at least one fluid line extending from the inlet to the outlet;
 an electrical current supply device; and a meltable component comprising a film and an electrical conductor, the film positioned between the first and second support plates such that it extends over at least a portion of the inner face and beyond the fluid line, wherein the electrical conductor is electrically coupled to the electrical current supply, and is modifiable from an initial state, in which measurement fluid flows through the fluid line flows, and an activated state, in which the electrical conductor melts a portion of the film thereby diverting measurement fluid away from the outlet.

27. The device for measuring blood sugar values according to claim 1, wherein the film extends over substantially the entire inner surface.

28. The device for measuring blood sugar values according to claim 1, wherein the film is a laminate.

29. The device for measuring blood sugar values according to claim 1, wherein the electrical conductor is integral with the film is formed on a surface of the film.

30. The device for measuring blood sugar values according to claim 1, wherein at least a portion of the electrical conductor is configured to melt upon an current passing therethrough.

31. The device for measuring blood sugar values according to claim 1, wherein an interface is defined by a portion of the first support plate that overlaps the second support plate, and wherein the film extends over substantially the entire interface.

32. The device for measuring blood sugar values according to claim 17, wherein the flow system and the fluid runoff are formed in an inner face of the first support plate.

33. The device for measuring blood sugar values according to claim 17, wherein the flow system is formed in an inner face of the first support plate and the fluid runoff is formed in an inner face of the second support plate.

34. The device for measuring blood sugar values according to claim 26, further comprising a control device and a pressure sensor adapted to measure the pressure of the fluid in the flow system, the control device being in electronic communication with the electrical current supply device and the pressure sensor, and wherein the control device is provided with programming instructions to receive signals from the pressure sensor and, based on the received signals, direct the electrical current supply device to supply current to the electrical conductor.

* * * * *